US008691668B2

(12) United States Patent
Gatineau et al.

(10) Patent No.: US 8,691,668 B2
(45) Date of Patent: Apr. 8, 2014

(54) DIHALIDE GERMANIUM(II) PRECURSORS FOR GERMANIUM-CONTAINING FILM DEPOSITIONS

(75) Inventors: Julien Gatineau, Tsuchiura (JP); Andreas Zauner, Voisins le Bretonneux (FR); Hana Ishii, Tsukuba (JP)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 13/393,975

(22) PCT Filed: Sep. 2, 2010

(86) PCT No.: PCT/IB2010/053961
§ 371 (c)(1),
(2), (4) Date: May 16, 2012

(87) PCT Pub. No.: WO2011/027321
PCT Pub. Date: Mar. 10, 2011

(65) Prior Publication Data
US 2012/0231611 A1 Sep. 13, 2012

Related U.S. Application Data

(60) Provisional application No. 61/239,348, filed on Sep. 2, 2009.

(51) Int. Cl.
*H01L 21/20* (2006.01)
(52) U.S. Cl.
USPC .................................. 438/478; 257/E21.09
(58) Field of Classification Search
USPC .................................. 438/478; 257/E21.09
See application file for complete search history.

(56) References Cited

U.S. PATENT DOCUMENTS

| 3,573,958 | A | 4/1971 | Small |
| 4,141,778 | A | 2/1979 | Domrachev et al. |
| 4,377,613 | A | 3/1983 | Gordon |
| 4,419,386 | A | 12/1983 | Gordon |
| 5,656,338 | A | 8/1997 | Gordon |
| 6,984,591 | B1 | 1/2006 | Buchanan et al. |
| 7,413,776 | B2 | 8/2008 | Shenai-Khatkhate et al. |
| 8,101,237 | B2 * | 1/2012 | Okubo et al. ............ 427/255.29 |
| 2006/0046521 | A1 | 3/2006 | Vaartstra et al. |
| 2006/0063394 | A1 | 3/2006 | McSwiney et al. |
| 2006/0138393 | A1 | 6/2006 | Seo et al. |
| 2006/0172067 | A1 | 8/2006 | Ovshinsky et al. |
| 2006/0172068 | A1 | 8/2006 | Ovshinsky |
| 2006/0180811 | A1 | 8/2006 | Lee et al. |
| 2006/0292301 | A1 | 12/2006 | Herner |
| 2007/0054475 | A1 | 3/2007 | Lee et al. |
| 2008/0003359 | A1 | 1/2008 | Gordon et al. |
| 2008/0026577 | A1 | 1/2008 | Shenai-Khatkhate et al. |
| 2008/0035906 | A1 | 2/2008 | Park et al. |
| 2008/0096386 | A1 | 4/2008 | Park et al. |
| 2008/0108174 | A1 | 5/2008 | Park et al. |
| 2009/0137100 | A1 | 5/2009 | Xiao et al. |
| 2009/0142881 | A1 | 6/2009 | Xiao et al. |
| 2009/0280052 | A1 | 11/2009 | Xiao et al. |
| 2009/0299084 | A1 | 12/2009 | Okubo et al. |

FOREIGN PATENT DOCUMENTS

| DE | 42 34 998 | 4/1994 |
| EP | 0 568 074 | 11/1993 |
| EP | 1 180 553 | 2/2002 |
| EP | 1 464 724 | 10/2004 |
| EP | 1 464 725 | 10/2004 |
| EP | 1 806 427 | 7/2007 |
| EP | 1 995 236 | 11/2008 |
| WO | WO 83 01018 | 3/1983 |
| WO | WO 96 40448 | 12/1996 |
| WO | WO 98 16667 | 4/1998 |
| WO | WO 00 23635 | 4/2000 |
| WO | WO 00 29637 | 5/2000 |
| WO | WO 01 66816 | 9/2001 |
| WO | WO 02 27063 | 4/2002 |
| WO | WO 03 083167 | 10/2003 |
| WO | WO 2007 062096 | 5/2007 |
| WO | WO 2007 067604 | 6/2007 |
| WO | WO 2007 133837 | 11/2007 |
| WO | WO 2008 002546 | 1/2008 |
| WO | WO 2008 008319 | 1/2008 |
| WO | WO 2008 057616 | 5/2008 |
| WO | WO 2009 039187 | 3/2009 |
| WO | WO 2009 081383 | 7/2009 |
| WO | WO 2009 132207 | 10/2009 |
| WO | WO 2010 055423 | 5/2010 |

OTHER PUBLICATIONS

Akkari, A. et al., "Three coordinate divalent Group 14 element compounds with an β-diketiminate as supporting ligand," J. of Organometallic Chemistry 622 (2001) 190-198.
Ayers, A. et al., "Azido derivatives of germanium(II) and tin(II): Syntheses and characterization of [(Mes)$_2$DAP]GeN$_3$, [(Mes)$_2$DAP]SnN$_3$, and the corresponding chloro analogues featuring heterocyclic six$\pi$-electron ring systems (where [(Mes)$_2$DAP]= {N(Mes)C(Me)}$_2$CH)," Inorg. Chem. 2001, 40, 1000-1005.
Chizmeshya, A.V.G. et al., "Synthesis of butane-like SiGe hydrides: Enabling precursors for CVD of Ge-rich semiconductors," J. Am .Chem. Soc. 2006, 128, 6919-6930.
Ding, Y. et al., "Synthesis and structures of monomeric divalent germanium and tin compounds containing a bulky diketiminato ligand," Organometallics 2001, 20, 1190-1194.
Du Mont, W.-W. et al., "α-Eliminierungsreaktionen an trihalogengermylphosphinen," Journal of Organometallic Chemistry, 128 (1977) 99-114.
Du Mont, W.-W. et al., "Triorganophosphan-dichlor- und -dibromgermandiyl und -stannandiyl: Phosphan-stabilisierte Ge$^{II}$- und Sn$^{II}$- Halogenide," Angew. Chem., vol. 88 (1976), No. 9, 303.

(Continued)

*Primary Examiner* — Luan C Thai
(74) *Attorney, Agent, or Firm* — Patricia E. McQueeney

(57) ABSTRACT

Disclosed are GeX$_2$L$_n$ molecules, with X being a halide, L being an adduct other than C$_4$H$_8$O$_2$, and 0.5≤n≤2. These molecules have lower melting points and/or increased volatility compared to GeCl$_2$-dioxane. Also disclosed is the use of such molecules for deposition of thin films, such as chalcogenide, SiGe, and GeO$_2$ films.

17 Claims, No Drawings

(56) References Cited

OTHER PUBLICATIONS

Jutzi, P. et al "Basenstabilisierte germylene. II. Darstellung und eigenschaftern von benzothiazol-dichlorgermylen (Base stabilized germylene. II. Preparation and properties of benzothiazole-dichlorogermylene)," Journal of Organometallic Chemistry, 1974, vol. 81, No. 3, pp. 341-350.

Jutzi, P. et al., "Stabilization of monomeric dichlorogermylene," Angew, Chem. Int'l, Edit. vol. 12 (1973), No. 12, 1002-1003.

Jutzi, P. et al., "Zur reaktivitat der Is-C-bindung in pyridylsilanen (On the reactivity of the silicon-carbon bond in pyridylsilanes)," Journal of Organometallic Chemisty, 1976, vol. 104, No. 2, pp. 153-160.

Kim, R.-Y. et al., "Structural properties of $Ge_2Sb_2Te_5$ thin films by metal organic chemical vapor deposition for phase change memory applications," Appl. Phys. Lett., 89, 102107-1-102107-3, 2006.

King, R.B. "Secondary and tertiary phosphine adducts of germanium(II) diode," Inorganic Chemistry, vol. 2, No. 1, Feb. 1963.

Kouvetakis, J. et al., "Synthesis and atomic and electronic structure of new Si-Ge-C alloys and compounds," Chem. Mater. 1998, 10, 2935-2949.

Lee, J. et al., "GeSbTe deposition for the PRAM application," Appl. Surf. Sci., 253, pp. 3969-3976, 2007.

Lee, V.Y. et al., "Redox properties of dihalogermylenes, dihalostannylenes and their complexes with Lewis bases," Journal of Organometallic Chemistry, 1995, vol. 499, No. 1-2, pp. 27-34.

Mironov, V.F. et al., "New method for preparing germanium dichloride and its use in syntheses of organogermanium compounds," Russian Journal of General Chemistry, vol. 64, No. 8, part 1, 1994, 1180.

Mironov, V.F. et al., "New routes to germanium dihalide dioxanates," Russian Journal of General Chemistry, vol. 64, No. 4, part 2, 1994, 633.

Nagendran, S. et al., "RGe(I)Ge(I)R compound (R=PhC(N$t$Bu)$_2$) with a Ge-Ge single bond and a comparison with the gauche conformation of hydrazine," Organometallics 2008, 27, 5459-5463.

Nefedov, O.M. et al., "Inorganic, organometallic, and organic analogues of carbenes," Angew. Chem. Int'l Edit., vol. 5 (1966), No. 12, 1021-1038.

Nefedov, O.M. et al., "Molecular complexes of germylene with η-donor ligands," Izv AKA Nauk Ser Khimi, 1980, 170-173.

Nefedov, O.M. et al., "New adducted complexes of dichlorogermanium," Bulletin of the Russian Academy of Sciences Division of Chemical Sciences, 1973, No. 12, 2824-2825.

Pacl, Z. et al., "Organogermanium compounds. X. The effect of structure on the basicity of ethyl(dimethylamijno)germanes," Collection Czechoslov, Chem. Commun. vol. 36, 1971.

Pore, V. et al., "Atomic layer deposition of metal tellurides and selenides using alkylsilyl compounds of tellurium and selenium," J. Am. Chem. Soc., DOI 10.1021/ja8090388, Nov. 18, 2008.

Razuvaev, G.A. et al, "Complex compound of dichloride germanium," Proceedings of the Academy of Sciences of the USSR, 1966, 584.

Razuvaev, G.A. et al., "Organosilicon and organogermanium derivatives with silicon-metal and germanium-metal bonds," Pure and Applied Chemistry, 1969, vol. 19, No. 3-4, pp. 353-374.

Ritala, M. et al., "Atomic layer deposition of $Ge_2Sb_2Te_5$ thin films," Microelectronic Engineering, Oct. 2009, vol. 86, No. 7-9, pp. 1946-1949.

Riviere, P. et al., "Germanium(II) and germanium(IV) compounds from elemental germanium," Organometallics 1991, 10, 1227-1228.

Shcherbinin, V.V. et al., "Methods for preparing germanium dihalides," Russian Journal of General Chemistry, vol. 68, No. 7, 1998, 1013-1016.

Woelk, E. et al., "Designing novel organogermanium OMVPE precursors for high-purity germanium films," Journal of Crystal Growth 287 (2006) 684-687.

"N-methyl morpholine," product specification, http://chemicalland21.com/industrialchem/functional%20Monomer/N-METHYL%20MORPHOLINE.htm, Sep. 1, 2010.

International Search Report and Written Opinion for corresponding PCT/IB2010/053961, Nov. 9, 2010.

Becker, G. et al., "Synthese, Struktur and Reaktivität des Lithium-[tris-trimethylsilyl]silyl]tellanids," Anorg. Allg. Chem., 1992, 613, pp. 7-18.

Bonasia, P.J. et al. "New reagents for the synthesis of compounds containing metal-tellurium bonds: sterically hindered silyltellurolate derivatives and the x-ray crystal structures of [(THF)2LiTeSi(SiMe3)3]2 and [(12-crown-4)2Li][TeSi(SiMe3)3]", J. Am. Chem. Soc., 1992, 114 (13), pp. 5209-5214.

Breunig, H.J. "Thermochromic molecules with bonds of Se or Te and Sb or Bi", Phosphorus and Sulfur, 1988, vol. 38, pp. 97-102.

Choi, B.J. et al., "Cyclic PECVD of $Ge_2Sb_2Te_5$ films using metal-lorganic sources". J. Electrochemical Soc., 154 (4), pp. H318-H324, 2007.

Choi, B.J. et al. "Plasma-enhanced atomic layer deposition of $Ge_2Sb_2Te_5$ films using metal-organic sources for Phase change RAM." ALD 2006 proceedings, p. 62, 2006.

Dabbousi, B.O. et al., "(Me$_3$Si)$_3$SiTeH: preparation, characterization, and synthetic utility of a remarkably stable tellurol," J. Am. Chem. Soc., 1991, 113, pp. 3186-3188.

Detty, M.R. et al., "Bis(trialkylsilyl) chalcogenides. 1. Preparation and reduction of group 6A oxides," J. Org. Chem., 1982, 47, pp. 1354-1356.

Drake, J.E. et al. "Studies of silyl and germyl group 6 species. 5. Silyl and germyl derivatives of methane- and benzenetellurols," Inorg. Chem. 1980, 19, pp. 1879-1883.

Eom, T. et al., "Atomic Layer Deposition of (GeTe2)x(Sb2Te3)y films for phase change memories," Proceedings of Seoul National University Conference, Feb. 16-18, 2011.

Glatz, F. et al. "Thermal CVD of amorphous germanium films from 2,5-bis(tert.-buty1)-2,5-diaza-1-germa-cyclopentane organometallic precursor". Mat. Res. Soc. Symp. Proc., 1994, vol. 336, pp. 541-545.

Gonzalez-Hernandez, et al. "Structure of oxygen-doped Ge:Sb:Te films." Thin Solid Films (2006), 503(1-2), 13-17.

Groshens, T.J. et al., "Low temperature MOCVD growth of V/VI materials via a Me$_3$SiNMe$_2$ elimination reaction." Thermoelectrics, 1996. Fifteen International Conference on Pasadena, CA, USA Mar. 26-29, 1996, New York, Mar. 26, 1996, pp. 430-434.

Gu et al. "Optical and structural properties of oxygen-doped and annealed Ge—Sb—Te— thin films." Chinese Journal of Lasers (2003), 30(12), 1110-1115.

Herrmann, W.A. et al. "Stable cyclic germanediyls ("cyclogermylenes"); Synthesis, structure, metal complexes, and thermolyses". Angew. Chem. Int. Ed. Engl., (1992) 31, No. 11, pp. 1485-1488.

Kim, et al. "Phase separation of a $Ge_2Sb_2Te_5$ alloy in the transition from an amorphous structure to crystalline structures." J. Vac. Sci. Technol. 929, 24(4), 2006.

Lappert, M.F. et al. "Monomeric, coloured germanium(II) and tin(II) di-t-butylamides, and the crystal and molecular structure of Ge(NCMe$_2$[CH$_2$]$_3$CMe$_2$)$_2$". J. Chemical Soc. Chem. Comm. 1980, pp. 621-622.

Naghavi, N. et al., "Growth studies and characterisation of In2S3 thin films deposited by atomic layer deposition (ALD)," Applied Surface Science 222 (2004), pp. 65-73.

Prokop, J. et al. "Selective deposition of amorphous germanium on Si with respect to SiO$_2$ by organometallic CVD". J. NonCryst. Solids, 198-200 (1996) pp. 1026-1028.

Wang, et al. "Influence of Sn doping upon the phase change characteristics of $Ge_2Sb_2Te_5$." Phys. Stat. Sol. (A) 3087-3095, 201(14), 2004.

International Search Report and Written Opinion for PCT/US2008/076698, Dec. 22, 2008.

International Search Report and Written Opinion for PCT/IB2008/055499, May 15, 2009.

International Search Report and Written Opinion for PCT/IB2009/008067, Jun. 1, 2010.

Singapore Written Opinion for SG 201008444-0, Jul. 1, 2011.

* cited by examiner

DIHALIDE GERMANIUM(II) PRECURSORS FOR GERMANIUM-CONTAINING FILM DEPOSITIONS

Cross Reference to Related Applications

This application is a 371 of International PCT Application PCT/IB2010/053961, filed Sep. 2, 2010, which claims priority to U.S. Provisional Application 61/239,348, filed Sep. 2, 2009, the entire contents of each being incorporated herein by reference.

TECHNICAL FIELD

Disclosed are germanium-containing precursors for use in the manufacture of semiconductor, photovoltaic, LCD-TFT, or flat panel type devices. Also disclosed are vapor deposition methods, preferably thermal ALD, using the germanium-containing precursors to form germanium-containing films.

BACKGROUND

Phase Change Memory (PCM) is a non-volatile memory commonly used in re-writable data storage media such as CDs and DVDs. The phenomenon relies on the property of chalcogenide materials to exhibit unlimited and reversible phase change between their amorphous and crystalline phase, each of theses phases having distinct optical and electrical properties. In electronic devices, each of these phases is associated to one bite (0 or 1), which enables data storage. The chalcogenide materials may have different compositions. The chalcogenide materials are frequently alloys made of tellurium, germanium, antimony, and/or selenium. $Ge_2Sb_2Te_5$ (GST) is one of the most studied chalcogenide materials. However, although the deposition of GST films using CVD or ALD technique has been reported, the search remains for adequate precursors and deposition processes suitable for the commercial deposition of GST.

GST films were obtained by Ritala and his team at 90° C. in thermal ALD mode using germanium, antimony, and tellurium precursors which exhibit a very high reactivity between each others (Ritala et al., Microelectronic Engineering 86 (2009) 1946-1949). $GeCl_2$-dioxane, $Te(SiEt_3)_2$ or $Te(SitBuMe_2)_2$ were used. The reaction that enables the deposition at low temperature was already hinted by Razuvaev (Razuvaev et al., Organosilicon and organogermanium derivatives with silicon-metal and germanium-metal bonds, 1969, Vol. 19, Issue 3, p. 353-374), and is as follows:

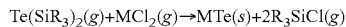

$$Te(SiR_3)_2(g) + MCl_2(g) \rightarrow MTe(s) + 2R_3SiCl(g)$$

In these articles, the poor quality of the films, as well as the use of a plasma power, which can damage the sub-layer and may not allow enough uniform coverage of patterned wafers, was a problem. The use of $GeCl_2$-dioxane may also be a problem as this molecule exhibits a high melting point (178-180° C.) and a low volatility, making it a less than ideal candidate for CVD/ALD deposition techniques.

WO2009/132207 to ASM International N.V. disclosed atomic layer deposition processes for forming Te-containing films, including Ge—Te and $Ge_2Sb_2Te_5$ (GST). The Ge-containing precursors used in the disclosed processes include $GeX_2$ with X being F, Cl, Br, or I and adducted derivatives of $GeX_2$, such as $GeCl_2$-dioxane. Exemplary depositions using $GeBr_2$ and $GeCl_2$-dioxane precursors are provided.

In most of the work published up to now, the poor quality of the films, as well as the use of a plasma power, which can damage the sub-layer and may not allow sufficiently uniform coverage of patterned wafers, is a problem. The use of $GeCl_2$-dioxane may also be a problem as this molecule exhibits a high melting point (178-180° C.), which raise handling as well as delivery issues, and volatility mismatch with the tellurium and antimony molecules.

Accordingly, there exists a need for materials which allow deposition of germanium-containing films through CVD and ALD techniques.

NOTATION AND NOMENCLATURE

Certain abbreviations, symbols, and terms are used throughout the following description and claims and include: the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclobutyl groups, cyclopentyl groups, cyclohexyl groups, etc.

The abbreviation "Me" refers to a methyl group; the abbreviation "Et" refers to an ethyl group; the abbreviation "Pr" refers to a propyl group; the abbreviation "nPr" refers to a chain propyl group; the abbreviation "iPr" refers to an isopropyl group; the abbreviation "Bu" refers to a butyl (n-butyl) group; the abbreviation "tBu" refers to a tert-butyl group; the abbreviation "sBu" refers to a sec-butyl group; the abbreviation "iBu" refers to an iso-butyl group; the abbreviation "Ph" refers to a phenyl group; the abbreviation "THF" refers to tetrahydrofuran; the abbreviation "THP" refers to tetrahydropyran; the abbreviation "TMEDA" refers to N,N,N',N'-tetramethylenediamine; and the abbreviation "NMM" refers to N-methylmorpholine.

The standard abbreviations of the elements from the periodic table of elements are used herein. It should be understood that elements may be referred to by these abbreviations (e.g., Ge refers to germanium, Te refers to Tellurium, Sb refers to antimony, etc).

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

SUMMARY

Disclosed are germanium-containing precursors having the formula:

$$GeX_2\text{-}L_n$$

wherein:
X is independently selected from the group consisting of F, Cl, Br, and I;
L is a Lewis base; and
$0.5 \leq n \leq 2$, preferably $0.75 \leq n \leq 1.25$,
provided that L is not $C_4H_8O_2$.

The disclosed precursors may include one or more of the following aspects:
  the Lewis base may be selected from the group consisting of water; ether; ketone; sulfoxide; carbon monoxide; benzene; dichloremethane; THF; THP, diglyme; pyridine; piperidine; pyrazine; TMEDA; NMM; trioxane; HOEt; $ER_3$ with E being P or As and R being a $C_2$ to $C_4$ alkyl group or Ph; and $ER^1R^2{}_2$ with E being P or As and $R^1$ being a $C_2$ to $C_4$ alkyl group, and $R^2$ being Ph; and
  the precursor may be selected from the group consisting of $GeCl_2$-(methyl-1,3-dioxane)$_n$, $GeCl_2$-(2,4-dimethyl-1,3-dioxane)$_n$, $GeCl_2$-(trioxane)$_n$, $GeCl_2$-(2-MeTHF)$_n$, $GeCl_2$-(THP)$_n$, $GeCl_2$—(HOEt)$_n$, $GeCl_2$-(diglyme)$_n$, $GeCl_2$—(PEtPh$_2$)$_n$, $GeCl_2$—(AsEt$_3$)$_n$, $GeCl_2$—(AsiPr$_3$)$_n$, $GeCl_2$—(AsnPr$_3$)$_n$, $GeCl_2$—(AsnBu$_3$)$_n$, $GeCl_2$—(AstBu$_3$)$_n$, $GeCl_2$—(AsEtPh$_2$)$_n$, $GeCl_2$-(methylpyridine)$_n$ $GeCl_2$-(trifluoromethylpyridine)$_n$, $GeCl_2$-(trimethylsilylpyridine)$_n$, $GeCl_2$-(1-methylpiperidine)$_n$, $GeCl_2$-(pyrazine)$_n$, $GeCl_2$-(2,6-dimethylpyrazine)$_n$, $GeCl_2$-(2-methoxypyrazine)$_n$, $GeCl_2$-(TMEDA)$_n$, $GeCl_2$—(NMM)$_n$, $GeCl_2$—(NEt$_3$)$_n$, $GeBr_2$-(methyl-1,3-dioxane)$_n$, $GeBr_2$-(2,4-dimethyl-1,3-dioxane)$_n$, $GeBr_2$-(trioxane)$_n$, $GeBr_2$-(THF)$_n$, $GeBr_2$-(2-MeTHF)$_n$, $GeBr_2$-(THP)$_n$, $GeBr_2$—(HOEt)$_n$, $GeBr_2$-(diglyme)$_n$, $GeBr_2$—(PEt$_3$)$_n$, $GeBr_2$-(PiPr$_3$)$_n$, $GeBr_2$-(PnPr$_3$)$_n$, $GeBr_2$-(PnBu$_3$)$_n$, $GeBr_2$—(PEtPh$_2$)$_n$, $GeBr_2$—(AsEt$_3$)$_n$, $GeBr_2$—(AsiPr$_3$)$_n$, $GeBr_2$—(AsnPr$_3$)$_n$, $GeBr_2$—(AsnBu$_3$)$_n$, $GeBr_2$—(AstBu$_3$)$_n$, $GeBr_2$—(AsPh$_3$)$_n$, $GeBr_2$—(AsEtPh$_2$)$_n$, $GeBr_2$-(pyridine)$_n$, $GeBr_2$-(methylpyridine)$_n$ $GeBr_2$-(trifluoromethylpyridine)$_n$, $GeBr_2$-(trimethylsilylpyridine)$_n$, $GeBr_2$-(1-methylpiperidine)$_n$, $GeBr_2$-(pyrazine)$_n$, $GeBr_2$-(2,6-dimethylpyrazine)$_n$, $GeBr_2$-(2-methoxypyrazine)$_n$, $GeBr_2$-(TMEDA)$_n$, $GeBr_2$—(NMM)$_n$, $GeBr_2$—(NEt$_3$)$_n$, $GeI_2$-(methyl-1,3-dioxane)$_n$, $GeI_2$-(2,4-dimethyl-1,3-dioxane)$_n$, $GeI_2$-(trioxane)$_n$, $GeI_2$-(THF)$_n$, $GeI_2$-(THP)$_n$, $GeI_2$-(2-MeTHF)$_n$, $GeI_2$—(HOEt)$_n$, $GeI_2$-(diglyme)$_n$, $GeI_2$—(PEt$_3$)$_n$, $GeI_2$-(PiPr$_3$)$_n$, $GeI_2$-(PnPr$_3$)$_n$, $GeI_2$—(PtBu$_3$)$_n$, $GeI_2$—(PPh$_3$)$_n$, $GeI_2$—(AsEt$_3$)$_n$, $GeI_2$—(AsiPr$_3$)$_n$, $GeI_2$—(AsnPr$_3$)$_n$, $GeI_2$—(AsnBu$_3$)$_n$, $GeI_2$—(AstBu$_3$)$_n$, $GeI_2$—(AsPh$_3$)$_n$, $GeI_2$—(AsEtPh$_2$)$_n$, $GeI_2$-(pyridine)$_n$, $GeI_2$-(methylpyridine)$_n$, $GeI_2$-(trifluoromethylpyridine)$_n$, $GeI_2$-(trimethylsilylpyridine)$_n$, $GeI_2$-(1-methylpiperidine)$_n$, $GeI_2$-(pyrazine)$_n$, $GeI_2$-(2,6-dimethylpyrazine)$_n$, $GeI_2$-(2-methoxypyrazine)$_n$, $GeI_2$-(TMEDA)$_n$, $GeI_2$—(NMM)$_n$, $GeI_2$—(NEt$_3$)$_n$, $GeF_2$-(methyl-1,3-dioxane)$_n$, $GeF_2$-(2,4-dimethyl-1.3-dioxane)$_n$, $GeF_2$-(trioxane)$_n$, $GeF_2$-(THF)$_n$, $GeF_2$-(2-MeTHF)$_n$, $GeF_2$-(THP)$_n$, $GeF_2$—(HOEt)$_n$, $GeF_2$-(diglyme)$_n$, $GeF_2$—(PEt$_3$)$_n$, $GeF_2$-(PiPr$_3$)$_n$, $GeF_2$-(PnPr$_3$)$_n$, $GeF_2$-(PnBu$_3$)$_n$, $GeF_2$—(PtBu$_3$)$_n$, $GeF_2$—(PPh$_3$)$_n$, $GeF_2$—(PEtPh$_2$)$_n$, $GeF_2$—(AsEt$_3$)$_n$, $GeF_2$—(AsiPr$_3$)$_n$, $GeF_2$—(AsnPr$_3$)$_n$, $GeF_2$—(AsnBu$_3$)$_n$, $GeF_2$—(AstBu$_3$)$_n$, $GeF_2$—(AsPh$_3$)$_n$, $GeF_2$—(AsEtPh$_2$)$_n$, $GeF_2$-(methylpyridine)$_n$, $GeF_2$-(trifluoromethylpyridine)$_n$, $GeF_2$-(trimethylsilylpyridine)$_n$, $GeF_2$-(1-methylpiperidine)$_n$, $GeF_2$-(α,α-bipyridine)$_n$, $GeF_2$-(pyrazine)$_n$, $GeF_2$-(2,6-dimethylpyrazine)$_n$, $GeF_2$-(2-methoxypyrazine)$_n$, $GeF_2$-(TMEDA)$_n$, $GeF_2$—(NMM)$_n$, $GeF_2$—(NEt$_3$)$_n$ and combinations thereof, preferably from the group consisting of $GeCl_2$—NMM, $GeCl_2$-methylpyridine, $GeCl_2$-2MeTHF, and combinations thereof.

Also disclosed is a method of forming a germanium-containing film on a substrate. The substrate is disposed in a reactor. The disclosed germanium-containing precursor is introduced into the reactor. The disclosed germanium-containing precursor reacts to form the germanium-containing film on the substrate. The disclosed method may include one or more of the following aspects:
  the germanium-containing precursor reacts with a second precursor;
  the second precursor being selected from the group consisting of tellurium-containing precursors, selenium-containing precursors, antimony-containing precursors, bismuth-containing precursors, indium-containing precursors, silicon-containing precursors, and combinations thereof;
  the second precursor being selected from the group consisting of Te(SiMe$_3$)$_2$, Te(SiEt$_3$)$_2$, Te(SiiPr$_3$)$_2$, Te(SitBu$_3$)$_2$, Te(SitBu$_2$Me)$_2$, Te(SitBuMe$_2$)$_2$, Te(GeMe$_3$)$_2$, Te(GeEt$_3$)$_2$, Te(GeiPr$_3$)$_2$, Te(GetBu$_3$)$_2$, Te(GetBu$_2$Me)$_2$, Te(GetBuMe$_2$)$_2$, TeMe$_2$, TeEt$_2$, TeiPr$_2$, TetBu$_2$, Te(N(SiMe$_3$)$_2$)$_2$, and combinations thereof;
  the second precursor being selected from the group consisting of SbCl$_3$, SbCl$_5$, SbCl$_3$-L' (L' being an adduct), SbMe$_3$, SbEt$_3$, Sb(iPr)$_3$, Sb(nPr)$_3$, Sb(tBu)$_3$, Sb(iBu)$_3$, Sb(NMe$_2$)$_3$, Sb(NEt$_2$)$_3$, Sb(N(SiMe$_3$)$_2$)$_3$, Sb(SiMe$_3$)$_3$, Sb(GeMe$_3$)$_3$, Sb(SiEt$_3$)$_3$, Sb(GeEt$_3$)$_3$, and combinations thereof;
  the second precursor being selected from the group consisting of SiH$_4$, Si$_2$H$_6$, Si$_3$H$_8$, N(SiH$_3$)$_3$, SiH$_2$Cl$_2$, SiCl$_4$, Si$_2$Cl$_6$, Si$_3$Cl$_8$, SiH$_2$(NEt$_2$)$_2$, combinations thereof, and radical species thereof;
  the germanium-containing precursor reacts with a co-reactant;
  the co-reactant being an oxygen source selected from the group consisting of O$_2$, O$_3$, H$_2$O, NO, NO$_2$, alcohols, combinations thereof, and radical species thereof;
  the co-reactant being a reducing agent selected from the group consisting of hydrogen, ammonia, amines, imines, hydrazines, silanes, and combinations thereof;
  the germanium-containing film comprising Ge, Sb, Te, Si, O, and combinations thereof;
  introducing a doping element to the germanium-containing film;
  the doping element is selected from the group consisting of silicon, nitrogen, and oxygen; and
  the substrate being selected from the group consisting of a metal layer and a metal nitride layer, preferably from the group consisting of a tungsten layer, a titanium nitride layer, and a titanium aluminum nitride layer.

DETAILED DESCRIPTION OF PREFERRED EMBODIMENTS

Disclosed herein are non-limiting embodiments of methods, apparatus, and compounds which may be used in the manufacture of semiconductor, photovoltaic, LCD-TFT, or flat panel type devices.

Disclosed are dihalide germylene precursors for the deposition of germanium-containing films (for example GeSbTe, Ge, SiGe, and GeO$_2$) by CVD/ALD processes at low temperature. The use of such precursors provides advantages over currently used precursors because the disclosed precursors are in the same oxidation state as the molecule deposited in the GST film. Additionally, the halide ligand may help to obtain alloy films at low temperatures. The germanium-containing film depositions may be carried out by thermal and/or plasma-enhanced CVD, ALD, and pulse CVD.

The disclosed $GeX_2$-L$_n$ precursors, with X being a halide, L being an adduct other than $C_4H_8O_2$, and $0.5 \leq n \leq 2$, have lower melting points than GeCl$_2$-dioxane. Also disclosed is the use of such precursors for deposition of thin films, such as chalcogenide, SiGe, GeO$_2$ films.

The general structure of the disclosed germylene halide precursors is:

$$GeX_2\text{-}L_n$$

wherein:
X is a halide selected from Cl, F, I, or Br;
L is a Lewis base other than C$_4$H$_8$O$_2$; and
0.5≤n≤2, preferably 0.75≤n≤1.25.

The Lewis base is selected so that the melting point of the resulting compound is lower than that of GeCl$_2$-dioxane and/or the volatility is higher. The Lewis base may be selected from:
Compounds containing N, P, As, Sb, and Bi and having an oxidation state of 3, such as pyridine; piperidine; pyrazine; N,N,N',N'-tetramethylenediamine (TMEDA); N-methylmorpholine (NMM); ER$_3$ with E being P or As and R being a C$_2$ to C$_4$ alkyl group or Ph; and ER$^1$R$^2{}_2$ with E being P or As and R$^1$ being a C$_2$ to C$_4$ alkyl group, and R$^2$ being Ph;
Compounds containing O, S, Se, and Te and having an oxidation state of 2, such as trioxane, substituted dioxanes, tetrahydrofuran (THF), tetrahydropyran (THP), diglyme, water, alcohols such as HOEt, ethers, ketones, sulfoxides; and
Molecules like carbon monoxide, aromatic hydrocarbons such as benzene, and dichloromethane.

Exemplary N—, P—, As—, Sb—, or Bi-containing Lewis bases having an oxidation state of 3 include but are not limited to pyridine, bipyridine (2,2-bipyridine or 4,4-bipyridine), pyridazine, pyrimidine, pyrazine, trialkylphosphine (PEt$_3$, PPr$_3$, P$^t$Bu$_3$, PPh$_3$, P$^t$BuMe$_2$), dialkylphosphine (PHEt$_2$, PH$^t$Bu$_2$, etc), alkylphosphine (PH$_2$Et, etc), trialkylarsine (AsEt$_3$, AsPr$_3$, AsBu$_3$, AsPh$_3$, As$^t$BuMe$_2$), dialkylarsine (AsHEt$_2$, AsHBu$_2$, etc), and alkylarsine (AsH$_2$Et, etc). Although N-methylmorpholine includes both oxygen and nitrogen, it is included in the N-containing group of compounds because the ether property of morpholine is typically inert, with the amine being involved in most chemical reactions (see, e.g., the abstract on N-methylmorpholine published on the internet at chemicalland21.com/industrialchem/functional%20Monomer/N-ETHYL%20MORPHOLINE.htm by Chemicalland21.com).

Any of the N—, P—, As—, Sb—, or Bi-containing Lewis bases may include substitution groups (on the carbon atoms for example). More particularly, linear or cyclic C$_1$-C$_4$ alkyl groups (including Me, Et, iPr, nPr, iBu, tBu, sBu) may be used as substitution groups. Some exemplary substituted nitrogen-containing compounds include methylpyridine and trifluoromethylpyridine, with the methyl of each compound being located at the 2-, 3-, or 4-position and trimethylsilylpyridine with the Si molecule being located at the 2-, 3-, or 4-position (i.e., 2-methylpyridine, 3-trifluoromethylpyridine, or 4-trimethylsilylpyridine).

Exemplary oxygen-containing Lewis bases having an oxidation state of 2 encompass ethers and ketones, which include but are not limited to alcohol, ethylene oxide, dimethyl ether, diethyl ether, dimethoxymethane, tetrahydrofuran, methoxybenzene, diglyme, triglyme, and tetraglyme.

Any of the O—, S—, Se—, or Te-containing Lewis bases may include substitution groups (on the carbon atoms for example). More particularly, linear or cyclic C$_1$-C$_4$ alkyl groups (including Me, Et, iPr, nPr, iBu, tBu, sBu), may be used as substitution groups. Exemplary substituted cyclic ethers include 2-methyltetrahydrofuran and methyl-1,3-dioxane, with the methyl substitution of the dioxane occurring at the 2, 4, 5, or 6 position (i.e. 2-methyl-1,3-dioxane, 4-methyl-1,3-dioxane, etc.).

The following molecules are known to exhibit a melting point lower than GeCl$_2$-dioxane:

TABLE 1

GeX$_2$-L$_n$ molecules with melting points lower than that of GeCl$_2$-dioxane

| Molecule GeX$_2$-L$_n$ | Melting point (° C.) |
| --- | --- |
| GeBr$_2$-dioxane | 170 |
| GeI$_2$—P(nBu)$_3$ | Liquid |
| GeI$_2$—PEtPh$_2$ | ~100 |
| GeCl$_2$-pyridine | 129-135 |
| GeCl$_2$-bypyridine | 174 |
| GeCl$_2$—PEt$_3$ | Liquid |
| 2GeCl$_2$—(C$_6$H$_4$)$_2$(CH$_2$)$_8$O$_6$ | 110-140 |
| GeCl$_2$—PPh$_3$ | 145-165 |
| GeCl$_2$—AsPh$_3$ | 129-132 |

Exemplary germanium-containing precursors include GeCl$_2$-(methyl-1,3-dioxane)$_n$, GeCl$_2$-(2,4-dimethyl-1,3-dioxane)$_n$, GeCl$_2$-(trioxane)$_n$, GeCl$_2$-(2-MeTHF)$_n$, GeCl$_2$-(THP)$_n$, GeCl$_2$—(HOEt)$_n$, GeCl$_2$-(diglyme)$_n$, GeCl$_2$—(PEtPh$_2$)$_n$, GeCl$_2$—(AsEt$_3$)$_n$, GeCl$_2$—(AsiPr$_3$)$_n$, GeCl$_2$—(AsnPr$_3$)$_n$, GeCl$_2$—(AsnBu$_3$)$_n$, GeCl$_2$—(AstBu$_3$)$_n$, GeCl$_2$—(AsEtPh$_2$)$_n$, GeCl$_2$-(methylpyridine)$_n$, GeCl$_2$-(trifluoromethylpyridine)$_n$, GeCl$_2$-(trimethylsilylpyridine)$_n$, GeCl$_2$-(1-methylpiperidine)$_n$, GeCl$_2$-(pyrazine)$_n$, GeCl$_2$-(2,6-dimethylpyrazine)$_n$, GeCl$_2$-(2-methoxypyrazine)$_n$, GeCl$_2$-(TMEDA)$_n$, GeCl$_2$—(NMM)$_n$, GeCl$_2$—(NEt$_3$)$_n$, GeBr$_2$-(methyl-1,3-dioxane)$_n$, GeBr$_2$-(2,4-dimethyl-1,3-dioxane)$_n$, GeBr$_2$-(trioxane)$_n$, GeBr$_2$-(THF)$_n$, GeBr$_2$-(2-MeTHF)$_n$, GeBr$_2$-(THP)$_n$, GeBr$_2$—(HOEt)$_n$, GeBr$_2$-(diglyme)$_n$, GeBr$_2$—(PEt$_3$)$_n$, GeBr$_2$-(PiPr$_3$)$_n$, GeBr$_2$-(PnPr$_3$)$_n$, GeBr$_2$-(PnBu$_3$)$_n$, GeBr$_2$—(PEtPh$_2$)$_n$, GeBr$_2$—(AsEt$_3$)$_n$, GeBr$_2$—(AsiPr$_3$)$_n$, GeBr$_2$—(AsnPr$_3$)$_n$, GeBr$_2$—(AsnBu$_3$)$_n$, GeBr$_2$—(AstBu$_3$)$_n$, GeBr$_2$—(AsPh$_3$)$_n$, GeBr$_2$—(AsEtPh$_2$)$_n$, GeBr$_2$-(pyridine)$_n$, GeBr$_2$-(methylpyridine)$_n$, GeBr$_2$-(trifluoromethylpyridine)$_n$, GeBr$_2$-(trimethylsilylpyridine)$_n$, GeBr$_2$-(1-methylpiperidine)$_n$, GeBr$_2$-(pyrazine)$_n$, GeBr$_2$-(2,6-dimethylpyrazine)$_n$, GeBr$_2$-(2-methoxypyrazine)$_n$, GeBr$_2$-(TMEDA)$_n$, GeBr$_2$—(NMM)$_n$, GeBr$_2$—(NEt$_3$)$_n$, GeI$_2$-(methyl-1,3-dioxane)$_n$, GeI$_2$-(2,4-dimethyl-1,3-dioxane)$_n$, GeI$_2$-(trioxane)$_n$, GeI$_2$-(THF)$_n$, GeI$_2$-(THP)$_n$, GeI$_2$-(2-MeTHF)$_n$, GeI$_2$—(HOEt)$_n$, GeI$_2$-(diglyme)$_n$, GeI$_2$—(PEt$_3$)$_n$, GeI$_2$-(PiPr$_3$)$_n$, GeI$_2$-(PnPr$_3$)$_n$, GeI$_2$—(PtBu$_3$)$_n$, GeI$_2$—(PPh$_3$)$_n$, GeI$_2$—(AsEt$_3$)$_n$, GeI$_2$—(AsiPr$_3$)$_n$, GeI$_2$—(AsnPr$_3$)$_n$, GeI$_2$—(AsnBu$_3$)$_n$, GeI$_2$—(AstBu$_3$)$_n$, GeI$_2$—(AsPh$_3$)$_n$, GeI$_2$—(AsEtPh$_2$)$_n$, GeI$_2$-(pyridine)$_n$, GeI$_2$-(methylpyridine)$_n$, GeI$_2$-(trifluoromethylpyridine)$_n$, GeI$_2$-(trimethylsilylpyridine)$_n$, GeI$_2$-(1-methylpiperidine)$_n$, GeI$_2$-(pyrazine)$_n$, GeI$_2$-(2,6-dimethylpyrazine)$_n$, GeI$_2$-(2-methoxypyrazine)$_n$, GeI$_2$-(TMEDA)$_n$, GeI$_2$—(NMM)$_n$, GeI$_2$—(NEt$_3$)$_n$, GeF$_2$-(methyl-1,3-dioxane)$_n$, GeF$_2$-(2,4-dimethyl-1.3-dioxane)$_n$, GeF$_2$-(trioxane)$_n$, GeF$_2$-(THF)$_n$, GeF$_2$-(2-MeTHF)$_n$, GeF$_2$-(THP)$_n$, GeF$_2$—(HOEt)$_n$, GeF$_2$-(diglyme)$_n$, GeF$_2$—(PEt$_3$)$_n$, GeF$_2$-(PiPr$_3$)$_n$, GeF$_2$-(PnPr$_3$)$_n$, GeF$_2$-(PnBu$_3$)$_n$, GeF$_2$—(PtBu$_3$)$_n$, GeF$_2$—(PPh$_3$)$_n$, GeF$_2$—(PEtPh$_2$)$_n$, GeF$_2$—(AsEt$_3$)$_n$, GeF$_2$—(AsiPr$_3$)$_n$, GeF$_2$—(AsnPr$_3$)$_n$, GeF$_2$—(AsnBu$_3$)$_n$, GeF$_2$—(AstBu$_3$)$_n$, GeF$_2$—(AsPh$_3$)$_n$, GeF$_2$—(AsEtPh$_2$)$_n$, GeF$_2$-(methylpyridine)$_n$, GeF$_2$-(trifluoromethylpyridine)$_n$, GeF$_2$-(trimethylsilylpyridine)$_n$, GeF$_2$-(1-methylpiperidine)$_n$, GeF$_2$-(α,α-bipyridine)$_n$, GeF$_2$-(pyrazine)$_n$, GeF$_2$-(2,6-dimethylpyrazine)$_n$, GeF$_2$-(2-methoxypyrazine)$_n$, GeF$_2$-(TMEDA)$_n$, GeF$_2$—(NMM)$_n$, GeF$_2$—(NEt$_3$)$_n$, or combinations thereof.

Preferably, the germanium-containing precursor is GeCl$_2$—NMM, GeCl$_2$-methylpyridine, GeCl$_2$-2MeTHF, and combinations thereof.

The synthesis of GeX$_2$-L$_n$ precursors (X, L, and n as described previously) that exhibit a lower melting point and/or a higher volatility than GeCl$_2$-dioxane is still on-going and the scope of this invention is therefore not limited to the molecules mentioned above, but to any molecule that fit the desired properties of physical state and volatility.

The disclosed precursors may be synthesized by adding the L adduct to a solution of GeCl$_2$-dioxane in anhydrous THF and stirring at room temperature. The mixture is filtered and any excess adduct and solvent as well as dioxane are distilled off in vacuum. The remaining product is crystallized in a vacuum exsiccator. The crystals obtained are washed repeatedly by anhydrous pentane and dried in vacuum.

Alternatively, the disclosed precursors may be synthesized using GeCl$_4$ as a starting material. 1,1,3,3-tetramethyldisiloxane is added to GeCl$_4$ and the L adduct is added to the mixture little by little and refluxed at 85° C. for 6 hours. The mixture is filtered and the crystals obtained are washed repeatedly by anhydrous pentane and dried under vacuum.

The germanium-containing films may be deposited using the disclosed precursors by any vapor deposition methods known to those of skill in the art. Examples of suitable deposition methods include without limitation Chemical Vapor Deposition (CVD), Low Pressure CVD (LPCVD), Plasma Enhanced CVD (PECVD), pulse PECVD, Atomic Layer Deposition (ALD), Plasma Enhanced ALD (PE-ALD), or combinations thereof. The plasma processes may utilize direct or remote plasma sources. Thermal CVD or ALD deposition methods may also be utilized. Preferably, the deposition process is thermal ALD.

The disclosed precursors may be supplied either in neat form or in a blend with a suitable solvent, such as ethyl benzene, xylenes, mesitylene, decane, or dodecane. The disclosed precursors may also be dissolved in a solvent that is identical to the precursor's Lewis base. The disclosed precursors may be present in varying concentrations in the solvent.

The neat or blended precursors are introduced into a reactor in vapor form. The precursors in vapor form may be produced by vaporizing the neat or blended precursor solution through a conventional vaporization step such as direct vaporization, distillation, or by bubbling. The neat or blended precursors may be fed in liquid state to a vaporizer where it is vaporized before it is introduced into the reactor. Alternatively, the neat or blended precursors may be vaporized by passing a carrier gas into a container containing the disclosed precursors or by bubbling the carrier gas into the disclosed precursors. The carrier gas may include, but is not limited to, Ar, He, N$_2$, and mixtures thereof. Bubbling with a carrier gas may also remove any dissolved oxygen present in the neat or blended precursor solution. The carrier gas and disclosed precursors are then introduced into the reactor as a vapor.

If necessary, the container containing the disclosed precursors may be heated to a temperature that permits the precursors to be in liquid phase and to have a sufficient vapor pressure. The container may be maintained at temperatures in the range of, for example, approximately 0° C. to approximately 150° C. Those skilled in the art recognize that the temperature of the container may be adjusted in a known manner to control the amount of precursor vaporized.

The reactor may be any enclosure or chamber within a device in which deposition methods take place such as, and without limitation, a parallel-plate type reactor, a cold-wall type reactor, a hot-wall type reactor, a single-wafer reactor, a multi-wafer reactor, or other types of deposition systems under conditions suitable to cause the precursors to react and form the layers.

The reactor contains one or more substrates onto which the thin films will be deposited. For example, the deposition chamber may contain from 1 to 200 silicon wafers having from 25.4 mm to 450 mm diameters. The one or more substrates may be any suitable substrate used in semiconductor, photovoltaic, flat panel or LCD-TFT device manufacturing. The one or more substrates may include any material that may be used as a heat source to liquefy the germanium-containing film when needed. An interface may be placed between the heat source and the germanium-containing layer in order to improve heat diffusion. Examples of suitable substrates include without limitation a metal layer or a metal nitride layer, silicon substrates, silica substrates, silicon nitride substrates, silicon oxy nitride substrates, tungsten substrates, titanium nitride, tantalum nitride, or combinations thereof. Additionally, substrates comprising tungsten or noble metals (e.g. platinum, palladium, rhodium or gold) may be used. The substrate may also be a layer deposited on a different material or may have one or more layers of differing materials already deposited on it from a previous manufacturing step. Preferably, when the resulting film is a chalcogenide film, the germanium-containing layer is deposited directly on a tungsten layer, a titanium nitride layer, or a titanium aluminum nitride layer.

The temperature and the pressure within the reactor are held at conditions suitable for the deposition process. For instance, the pressure in the reactor may be held between about 0.01 Torr and about 1,000 Torr, preferably between about 0.1 Torr and 100 Torr, as required by the deposition parameters. Likewise, the temperature in the reactor may be held between about 10° C. and about 350° C., preferably between about 25° C. and about 200° C., and more preferably between about 25° C. and about 150° C.

The germanium-containing precursors are reacted with one or more co-reactants and/or second precursors in order to deposit the germanium-containing film on at least one substrate in the reactor.

The co-reactants may be an oxygen source, such as oxygen, ozone, water, hydrogen peroxide, nitric oxide, nitrogen dioxide, alcohols, carboxylic acids, combinations thereof, or radical species thereof. Alternatively, the co-reactants may be a reducing gas, such as hydrogen, ammonia, amines, imines, hydrazines, silanes (e.g. SiH$_4$, Si$_2$H$_6$, Si$_3$H$_8$), alkyl silanes containing a Si—H bond (e.g. SiH$_2$Me$_2$, SiH$_2$Et$_2$), N(SiH$_3$)$_3$, and combinations thereof. Preferably the co-reactant is H$_2$ or NH$_3$. For example, without being bound by theory, Applicants believe that the use of a NH$_3$ reducing gas during CVD deposition may produce films having smaller grain size.

The co-reactants may be treated by plasma in order to decompose the co-reactants into radical form. For instance, the plasma may be generated with a power ranging from about 50 W to about 500 W, preferably from about 100 W to about 200 W. The plasma may be generated or present within the reactor itself. Alternatively, the plasma may generally be at a location removed from the reaction chamber, for instance, in a remotely located plasma system. One of skill in the art will recognize methods and apparatus suitable for such plasma treatment. For example, as discussed in the background, one of ordinary skill in the art will recognize that plasma treatment may not be suitable for sensitive sub-layers and/or films deposition on substrates having high aspect ratios. A plasma treatment may also be applied after the film deposition, whether the film deposition was performed in plasma mode or not, in order to improve the film characteristics (decrease impurities levels, increase density, etc.). The disadvantages for this method remain the same as when film deposition step is performed (i.e. damaging to sensitive sublayers and non-uniformity for substrates having high aspect ratios).

The co-reactants may be introduced into the reactor at the same time as, prior to, or subsequent to introduction of the germanium-containing precursor, or any combination of those introductions. The disclosed precursors and the co-reactants react to form a germanium-containing film on the substrate. Without being bound by theory, Applicants believe that the co-reactants may enhance the nucleation of the germanium-containing precursors at the surface of the substrate, which may result in higher quality germanium-containing films. Similarly, when deposition conditions permit, Applicants further believe that plasma-treating the co-reactants may provide the co-reactants with the energy needed to react with the germanium-containing precursors at lower temperatures.

The second precursors may be tellurium-containing precursors, selenium-containing precursors, antimony-containing precursors, bismuth-containing precursors, indium-containing precursors, silicon-containing precursors, or combinations thereof. Like the disclosed precursors, the second precursors may be supplied either in neat form or in a blend with a suitable solvent, such as ethyl benzene, xylenes, mesitylene, decane, or dodecane.

Exemplary tellurium-containing precursors include Te(SiMe$_3$)$_2$, Te(SiEt$_3$)$_2$, Te(SiiPr$_3$)$_2$, Te(SitBu$_3$)$_2$, Te(SitBu$_2$Me)$_2$, Te(SitBuMe$_2$)$_2$, Te(GeMe$_3$)$_2$, Te(GeEt$_3$)$_2$, Te(GeiPr$_3$)$_2$, Te(GetBu$_3$)$_2$, Te(GetBu$_2$Me)$_2$, Te(GetBuMe$_2$)$_2$, TeMe$_2$, TeEt$_2$, TeiPr$_2$, TetBu$_2$, Te(N(SiMe$_3$)$_2$)$_2$, or combinations thereof.

Exemplary antimony-containing precursors include SbCl$_3$, SbCl$_5$, SbCl$_3$-L' (L' being an adduct), SbMe$_3$, SbEt$_3$, Sb(iPr)$_3$, Sb(nPr)$_3$, Sb(tBu)$_3$, Sb(iBu)$_3$, Sb(NMe$_2$)$_3$, Sb(NEt$_2$)$_3$, Sb(N(SiMe$_3$)$_2$)$_3$, Sb(SiMe$_3$)$_3$, Sb(GeMe$_3$)$_3$, Sb(SiEt$_3$)$_3$, Sb(GeEt$_3$)$_3$, or combinations thereof.

Exemplary silicon-containing precursors include SiH$_4$, Si$_2$H$_6$, Si$_3$H$_8$, N(SiH$_3$)$_3$, SiH$_2$Cl$_2$, SiCl$_4$, Si$_2$Cl$_6$, Si$_3$Cl$_8$, SiH$_2$(NEt$_2$)$_2$, combinations thereof, and radical species thereof.

Without being bound by theory, Applicants believe that the following reaction between the disclosed precursors and the second precursors may produce the germanium-containing film:

$$(M^1R_3)_2M^2 + GeX_2\text{-}L_n \rightarrow 2R_3M^1X_2 + M^2Ge + nL,$$

wherein $M^1$=Si, Ge, or Sn, $M^2$=S, Se, or Te, each R is independently an alkyl group, and X=Cl, Br, I, or F. Similarly, Applicants believe that this reaction may provide for the deposition of germanium-containing films at lower temperatures. Although one of ordinary skill in the art will recognize that GeX$_2$ may substitute for GeX$_2$-L$_n$, the GeX$_2$ compounds are not stable enough to be used in the disclosed vapor deposition methods.

Depending on what type of film is desired to be deposited, one or more metal-containing precursors may be introduced into the reactor. The metal-containing precursors may include another metal source, such as Ti, Ta, Hf, Zr, Pb, Nb, Mg, Al, Sr, Y, Ba, Ca, Cu, Mn, Ru, lanthanides, and combinations thereof. Where a metal-containing precursor is utilized, the resultant film deposited on the substrate may contain at least two different metal types.

A doping element, such as silicon, nitrogen, or oxygen, may also be introduced into the germanium-containing film by methods known in the art. The doping elements may diffuse into the film, occupying holes or cavities. Alternatively, the doping elements may replace molecules already present in the film.

The disclosed precursors and/or co-reactants and/or second precursors and/or metal-containing precursors and/or doping elements (hereinafter, collectively referred to as the "reactants") may be introduced into the reactor simultaneously (CVD), sequentially (ALD), or in other combinations. The reactants may be mixed together to form a reactant mixture, and then introduced to the reactor in mixture form. Alternatively, the reactants may be sequentially introduced into the reaction chamber and purged with an inert gas between each introduction. In another alternative, the introductions may incorporate elements from both of the above-mentioned schemes. One of ordinary skill in the art will recognize that specific process requirements (e.g., shorter deposition time and faster film growth rate versus film uniformity) will determine the suitability of the different introduction methods.

For example, the disclosed precursors may be introduced in one pulse and two additional second precursors may be introduced together in a separate pulse [modified PE-ALD]. Alternatively, the reactor may already contain the co-reactant species prior to introduction of the disclosed precursors, the introduction of which may optionally be followed by a second introduction of the co-reactant species. In another alternative, the disclosed precursors may be introduced to the reactor continuously while the second precursors, metal-containing precursors, and/or doping agents are introduced by pulse (pulse PECVD). In yet another alternative, some of the reactants may be introduced simultaneously, either individually or as a mixture, and some of the reactants may be introduced sequentially. In each example, an introductory pulse may be followed by a purge or evacuation step to remove excess amounts of the component introduced. In each example, the pulse may last for a time period ranging from about 0.01 seconds to about 10 seconds, alternatively from about 0.3 seconds to about 5 seconds, alternatively from about 0.5 seconds to about 2 seconds.

Depending on the particular process parameters, deposition may take place for a varying length of time. Generally, deposition may be allowed to continue as long as desired or necessary to produce a film with the necessary properties. Typical film thicknesses may vary from several hundred angstroms to several hundreds of microns, depending on the specific deposition process. The deposition process may also be performed as many times as necessary to obtain the desired film.

In one non-limiting exemplary PE-ALD type process, the vapor phase of the disclosed precursor (for example, Ge—Cl$_2$—NMM) is introduced into the reactor, where it is contacted with a suitable substrate. Excess precursor may then be removed from the reactor by purging and/or evacuating the reactor. A second precursor (for example, Te(SiMe$_3$)$_2$) is introduced into the reactor where it reacts with the absorbed precursor in a self-limiting manner. Any excess second precursor is removed from the reactor by purging and/or evacuating the reactor. If the desired film is a GeTe film, this two-step process may provide the desired film thickness or may be repeated until a film having the necessary thickness has been obtained.

Alternatively, if the desired film is a GST film, the two-step process above may be followed by introduction of the vapor of a different second precursor (the "third precursor") (for example, SbCl$_3$) into the reactor. After introduction into the reactor, the third precursor is contacted with the GeTe film.

Any excess third precursor is removed from the reactor by purging and/or evacuating the reactor. Once again, a tellurium-containing precursor, which may be the same or difference from the second precursor (referred to here for convenience as the "second precursor") may be introduced into the reactor to react with the third precursor. Excess second precursor is removed from the reactor by purging and/or evacuating the reactor. If a desired film thickness has been achieved, the process may be terminated. However, if a thicker film is desired, the entire four-step process may be repeated. By alternating the provision of the disclosed precursor, second precursor, and third precursor, a film of desired composition and thickness can be deposited.

The germanium-containing films or layers resulting from the processes discussed above may include a pure metal (Ge), metal silicate ($Ge_kSi_l$), metal oxide ($Ge_nO_m$), metal oxynitride ($Ge_xN_yO_z$), or a GeSbTe film wherein k, l, m, n, x, y, and z are integers which inclusively range from 1 to 6. One of ordinary skill in the art will recognize that by judicial selection of the appropriate disclosed precursor, second precursors, and/or co-reactant species, the desired film composition may be obtained.

EXAMPLES

The following non-limiting examples are provided to further illustrate embodiments of the invention. However, the examples are not intended to be all inclusive and are not intended to limit the scope of the inventions described herein.

Example 1

Synthesis of $GeCl_2$-Adduct

The molecules in the table below were synthesized. To a solution of $GeCl_2$-dioxane in anhydrous THF, the L adduct was added and stirred at room temperature. The mixture is filtered and excess L adduct and solvent as well as dioxane are distilled off in vacuum. Remaining product crystallizes in a few hours in vacuum exsiccator. Obtained crystals are washed repeatedly by anhydrous pentane and dried in vacuum. These reactions gave quantitative yield.

| Molecule | MP ° C. | Volatility (1 Torr at T) |
| --- | --- | --- |
| $GeCl_2$-2-methylpyridine | 54.4 | 145° C. |
| $GeCl_2$-3-methylpyridine | oil | 155° C. |
| $GeCl_2$-4-methylpyridine | 66.9 | 165° C. |
| $GeCl_2$-2-(trimethylsilyl)pyridine | 69 | 140° C. |
| $GeCl_2$-NMM | 78.8 | 130° C. |
| $GeCl_2$-1-Methylpiperidine | oil | 135° C. |

The newly synthesized molecules have a melting point lower than $GeCl_2$-dioxane (178-180° C.), which is important for the ease of delivery of the molecule to the reaction chamber.

Example 2

Prophetic Deposition of GST Films Using dichlorogermanium(II)-2-methylpyridine

Applicants believe that Germanium Antimony Tellurium (GST) films may be deposited from temperatures as low as 70° C. in thermal mode. The antimony and tellurium precursors may be $SbCl_3$ and $Te(SitBuMe_2)_2$, respectively. The germanium molecule may be $GeCl_2$-2-methylpyridine. Vapors of the different compounds will be delivered to a reaction furnace using $N_2$ as a carrier gas, as well as for dilution purpose. The introduction of each precursor may be made separately, and followed by purge to avoid any gas-phase reaction between each of them (ALD mode). In particular, the delivery line of vapors of $GeCl_2$-2-methylpyridine may be heated at 150° C. in order to avoid any solidification and adsorption of the molecule on the delivery line.

In such conditions, GST films are expected to be obtained in thermal mode at temperatures from 70° C. Deposition in deep trench structures may be obtained with step coverage above 90% in holes of aspect ratio higher than 10 to 1.

The concentrations of various non GST elements into the deposited metal films will be analyzed by an Auger spectrometry and the values for all elements (carbon, nitrogen, oxygen) are expected to be below the detection limit of the apparatus. The composition of the film may be tuned in function of each precursor's introduction time and deposition temperature.

Example 3

Prophetic Deposition of GST Films Using dichlorogermanium(II)-dioxane

All conditions will be similar to those of Example 2, with the exception that the prior art precursor $GeCl_2$-dioxane will be used instead of $GeCl_2$-2-methylpyridine. As the melting point of $GeCl_2$-dioxane is around 40° C. higher than $GeCl_2$-2-methylpyridine, it will be necessary to heat the lines at least 40° C. higher to obtain the same effect (no solidification in the lines). Using such high temperatures will prove problematic for system set-up, as not only a high thermal budget will be required, but high-temperature valves will be necessary, increasing the burden on the budget.

Example 4

Prophetic Deposition of SiGe Films Using $GeCl_2$-2-methylpyridine

Silicon-Germanium (SiGe) films may be deposited at temperatures as low as 200° C. in thermal mode without the use of a co-reactant. The silicon precursor may be $SiHMe_3$. The germanium molecule may be $GeCl_2$-2-Methylpyridine. Vapors of the different compounds will be delivered to a reaction furnace as a gas for $SiHMe_3$ or using $N_2$ as a carrier gas in a bubbler type of delivery for $GeCl_2$-2-methylpyridine. $N_2$ will also be used for dilution purpose. The introduction of each precursor will be made separately, and followed by a purge to avoid any gas-phase reaction between the two molecules (ALD mode). In particular, the delivery line of vapors of $GeCl_2$-2-methylpyridine will be heated to 130° C. in order to allow a quick purging of the lines and prevent the molecule from adsorption on the tube.

In such conditions, SiGe films are expected to be obtained in thermal mode at temperatures from 200° C. Depositions in plasma mode may allow depositions of films at slightly lower temperatures (from 150° C.). Deposition in deep trench structures may be obtained with step coverage above 90% in holes of aspect ratio higher than 10 to 1.

The concentrations of various non SiGe elements into the deposited films will be analyzed by an Auger spectrometry and the values for all elements (carbon, nitrogen, oxygen) are expected to be below the detection limit of the spectrometer.

Example 5

Prophetic Deposition of GeO$_2$ Films Using GeCl$_2$-2-methylpyridine

Germanium oxide (GeO$_2$) films may be deposited from 200° C. in thermal mode. The oxygen source may be O$_2$. The germanium molecule may be GeCl$_2$-2-Methylpyridine. Vapors of GeCl$_2$-2-methylpyridine will be transported to the reaction furnace using a bubbling delivery technique and nitrogen (N$_2$) as a carrier gas. N$_2$ may also be used for dilution purpose. The introduction of each precursor will be made separately, and followed by purge to avoid any gas-phase reaction between the two molecules (ALD mode). In particular, the delivery line of vapors of GeCl$_2$-2-methylpyridine will be heated to 130° C. in order to allow a quick purging of the lines and prevent the molecule from adsorption on the tube.

In such conditions, GeO$_2$ films are expected to be obtained in thermal mode at temperatures from 200° C. Depositions in plasma mode may allow depositions of films at slightly lower temperatures (from 150° C.), with improved film properties. Deposition in deep trench structures may be obtained with step coverage above 90% in holes of aspect ratio higher than 10 to 1.

The concentrations of impurities (carbon, nitrogen, chlorine) will be analyzed by an Auger spectrometry and the values for all elements are expected to be below the detection limit of the apparatus.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. A method of forming a germanium-containing film, the method comprising:
   providing a reactor having a substrate disposed therein;
   introducing into the reactor a germanium-containing precursor having the formula:

   $$GeX_2\text{-}L_n$$

wherein:
   X is independently selected from the group consisting of F, Cl, Br, and I;
   L is a Lewis base; and
   $0.5 \leq n \leq 2$, preferably $0.75 \leq n \leq 1.25$,
   provided that L is not C$_4$H$_8$O$_2$; and
   reacting the germanium-containing precursor to form the germanium-containing film on the substrate.

2. The method of claim 1, wherein the Lewis base is selected from the group consisting of water; ether; ketone; sulfoxide; carbon monoxide; benzene; dichlormethane; THF; THP; digiyme; pyridine; piperidine; pyrazine; TMEDA; NMM; trioxane; HOEt; ER$_3$ with E being P or As and R being a C$_2$ to C$_4$ alkyl group or Ph; and ER$^1$R$^2$ with E being P or As and R$^1$ being a C$_2$ to C$_4$ alkyl group and R$^2$ being Ph.

3. The method of claim 1, wherein the germanium-containing precursor is selected from the group consisting of GeCl$_2$-(methyl-1,3-dioxane)$_n$, GeCl$_2$-(2,4-dimethyl-1,3-dioxane)$_n$, GeCl$_2$-(trioxane)$_n$, GeCl$_2$-(2-MeTHF)$_n$, GeCl$_2$-(THP)$_n$, GeCl$_2$—(HOEt)$_n$, GeCl$_2$-(diglyme)$_n$, GeCl$_2$—(PEt$_3$)$_n$, GeCl$_2$—(AsEt$_3$)$_n$, GeCl$_2$-(AsiPr$_3$)$_n$, GeCl$_2$-(AsnPr$_3$)$_n$, GeCl$_2$-(AsnBu$_3$)$_n$, GeCl$_2$-(AstBu$_3$)$_n$, GeCl$_2$—(AsEtPh$_2$)$_n$, GeCl$_2$-(methylpyridine)$_n$, GeCl$_2$-(trifluoromethylpyridine)$_n$, GeCl$_2$-(trimethylsilylpyridine)$_n$, GeCl$_2$-(1-methylpiperidine)$_n$, GeCl$_2$-(pyrazine)$_n$, GeCl$_2$-(2,6-dimethylpyrazine)$_n$, GeCl$_2$-(2-methoxypyrazine)$_n$, GeCl$_2$-(TMEDA)$_n$, GeCl$_2$—(NMM)$_n$, GeCl$_2$—(NEt$_3$)$_n$, GeBr$_2$-(methyl-1,3-dioxane)$_n$, GeBr$_2$-(2,4-dimethyl-1,3-dioxane)$_n$, GeBr$_2$-(trioxane)$_n$, GeBr$_2$-(THF)$_n$, GeBr$_2$-(2-MeTHF)$_n$, GeBr$_2$-(THP)$_n$, GeBr$_2$—(HOEt)$_n$, GeBr$_2$-(diglyme)$_n$, GeBr$_2$—(PEt$_3$)$_n$, GeBr$_2$-(PiPr$_3$)$_n$, GeBr$_2$-(PnPr$_3$)$_n$, GeBr$_2$-(PnBu$_3$)$_n$, GeBr$_2$—(PEtPh$_2$)$_n$, GeBr$_2$—(AsEt$_3$)$_n$, GeBr$_2$-(AsiPr$_3$)$_n$, GeBr$_2$-(AsnPr$_3$)$_n$, GeBr$_2$-(AsnBu$_3$)$_n$, GeBr$_2$-(AstBu$_3$)$_n$, GeBr$_2$—(AsPh$_3$)$_n$, GeBr$_2$—(AsEtPh$_2$)$_n$, GeBr$_2$-(pyridine)$_n$, GeBr$_2$-(methylpyridine)$_n$, GeBr$_2$-(trifluoromethylpyridine)$_n$, GeBr$_2$-(trimethylsilylpyridine)$_n$, GeBr$_2$-(1-methylpiperidine)$_n$, GeBr$_2$-(pyrazine)$_n$, GeBr$_2$-(2,6-dimethylpyrazine)$_n$, GeBr$_2$-(2-methoxypyrazine)$_n$, GeBr$_2$-(TMEDA)$_n$, GeBr$_2$—(NMM)$_n$, GeBr$_2$—(NEt$_3$)$_n$, GeI$_2$-(methyl-1,3-dioxane)$_n$, GeI$_2$-(2,4-dimethyl-1,3-dioxane)$_n$, GeI$_1$-(trioxane)$_n$, GeI$_1$-(THF)$_n$, GeI$_2$-(THP)$_n$, GeI$_2$-(2-MeTHF)$_n$, GeI$_2$—(HOEt)$_n$, GeI$_2$-(diglyme)$_n$, GeI$_2$—(PEt$_3$)$_n$, GeI$_2$-(PiPr$_3$)$_n$, GeI$_2$-(PnPr$_3$)$_n$, GeI$_2$—(PtBu$_3$)$_n$, GeI$_2$—(PPh$_3$)$_n$, GeI$_2$—(AsEt$_3$)$_n$, GeI$_I$-(AsiPr$_3$)$_n$, GeI$_2$-(AsnPr$_3$)$_n$, GeI$_2$-(AsnBu$_3$)$_n$, GeI$_2$-(AstBu$_3$)$_n$, GeI$_2$—(AsPh$_3$)$_n$, GeI$_I$—(AsEtPh$_2$)$_n$, GeI$_2$-(pyridine)$_n$, GeI$_2$-(methylpyridine)$_n$, GeI$_2$-(trifluoromethylpyridine)$_n$, GeI$_2$-(trimethylsilylpyridine)$_n$, GeI$_2$-(1-methylpiperidine)$_n$, GeI$_2$-(pyrazine)$_n$, GeI$_2$-(2,6-dimethylpyrazine)$_n$, GeI$_2$-(2-methoxypyrazine), GeI$_2$-(TMEDA)$_n$, GeI$_2$—(NMM)$_n$, GeI$_2$—(NEt$_3$)$_n$, GeF$_2$-(methyl-1,3-dioxane)$_n$, GeF$_2$-(2,4-dimethyl-1.3-dioxane)$_n$, GeF$_2$-(trioxane), GeF$_2$-(THF)$_n$, GeF$_2$-(2-MeTHF)$_n$, GeF$_2$-(THP)$_n$, GeF$_2$—(HOEt)$_n$, GeF$_2$-(diglyme)$_n$, GeF$_2$—(PEt$_3$)$_n$, GeF$_2$-(PiPr$_3$)$_n$, GeF$_2$-(PnPr$_3$)$_n$, GeF$_2$-(PnBu$_3$), GeF$_2$—(PtBu$_3$)$_n$, GeF$_2$—(PPh$_3$)$_n$, GeF$_2$—(PEtPh$_2$)$_n$, GeF$_2$—(AsEt$_3$), GeF$_2$-(AsiPr$_3$)$_n$, GeF$_2$-(AsnPr$_3$)$_n$, GeF$_2$-(AsnBu$_3$)$_n$, GeF$_2$-(AstBu$_3$)$_n$, GeF$_2$—(AsPh$_3$)$_n$, GeF$_2$—(AsEtPh$_2$)$_n$, GeF$_2$-(methylpyridine)$_n$, GeF$_2$-(trifluoromethylpyridine)$_n$, GeF$_2$-(trimethylsilylpyridine)$_n$, GeF$_2$-(1-methylpiperidine)$_n$, GeF$_2$-(α,α-bipyridine)$_n$, GeF$_2$-(pyrazine)$_n$, GeF$_2$-(2,6-dimethylpyrazine)$_n$, GeF$_2$-(2-methoxypyrazine)$_n$, GeF$_2$-(TMEDA)$_n$, GeF$_2$—(NMM)$_n$, GeF$_2$—(NEt$_3$)$_n$ and combinations thereof, preferably from the group consisting of GeCl$_2$—NMM, GeCl$_2$-methylpyridine, GeCl$_2$-2MeTHF, and combinations thereof.

4. The method of claim 1, wherein the germanium-containing precursor is GeCl$_2$-2-methylpyridine.

5. The method of claim 1, wherein the germanium-containing precursor is reacted with a second precursor.

6. The method of claim 5, wherein the second precursor is selected from the group consisting of a tellurium-containing precursor, a selenium-containing precursor, an antimony-containing precursor, a bismuth-containing precursor, an indium-containing precursor, a silicon-containing precursor, and combinations thereof.

7. The method of claim 5, wherein the second precursor is selected from the group consisting of Te(SiMe$_3$)$_2$, Te(SiEt$_3$)$_2$, Te(SiiPr$_3$)$_2$, Te(SitBu$_3$)$_2$, Te(SitBu$_2$Me)$_2$, Te(SitBuMe$_2$)$_2$, Te(GeMe$_3$)$_2$, Te(GeEt$_3$)$_2$, Te(GeiPr$_3$)$_2$, Te(GetBu$_3$)$_2$, Te(GetBu$_2$Me)$_2$, Te(GetBuMe$_2$)$_2$, TeMe$_2$, TeEt$_2$, TeiPr$_2$, TetBu$_2$, Te(N(SiMe$_3$)$_2$)$_2$, and combinations thereof.

8. The method of claim 5, wherein the second precursor is selected from the group consisting of SbCl$_3$, SbCl$_5$, SbCl$_3$-L' (L' being an adduct), SbMe$_3$, SbEt$_3$, Sb(iPr)$_3$, Sb(nPr)$_3$, Sb(tBu)$_3$, Sb(iBu)$_3$, Sb(NMe$_2$)$_3$, Sb(NEt$_2$)$_3$, Sb(N(SiMe$_3$)$_2$)$_3$, Sb(SiMe$_3$)$_3$, Sb(GeMe$_3$)$_3$, Sb(SiEt$_3$)$_3$, Sb(GeEt$_3$)$_3$, and combinations thereof.

9. The method of claim 5, wherein the second precursor is selected from the group consisting of SiH$_4$, Si$_2$H$_6$, Si$_3$H$_8$, $N(SiH_3)_3$, $SiH_2Cl_2$, $SiCl_4$, $Si_2Cl_6$, $Si_3Cl_8$, $SiH_2(NEt_2)_2$, combinations thereof, and radical species thereof.

10. The method of claim 5, wherein the germanium-containing film comprises Ge, Sb, Te, Si, O, and combinations thereof.

11. The method of claim 5, wherein the germanium-containing film comprises Ge, Sb, and Te.

12. The method of claim 5, wherein the germanium-containing film comprises Ge and Si.

13. The method of claim 1, wherein the germanium-containing precursor is reacted with a co-reactant.

14. The method of claim 13, wherein the co-reactant is an oxygen source selected from the group consisting of $O_2$, $O_3$, $H_2O$, NO, $NO_2$, alcohols, combinations thereof, and radical species thereof.

15. The method of claim 13, wherein the co-reactant is a reducing agent selected from the group consisting of hydrogen, ammonia, amines, imines, hydrazines, silanes, and combinations thereof.

16. The method of claim 1, further comprising introducing a doping element to the germanium-containing film, wherein the doping element is selected from the group consisting of silicon, nitrogen, and oxygen.

17. The method of claim 1, wherein the substrate is selected from the group consisting of a metal layer and a metal nitride layer, preferably from the group consisting of a tungsten layer, a titanium nitride layer, and a titanium aluminum nitride layer.

* * * * *